United States Patent [19]

Shillington

[11] Patent Number: 4,667,821
[45] Date of Patent: May 26, 1987

[54] SWIVEL TOP CLOSURE FOR PHLEBOTOMY CONTAINER

[75] Inventor: Richard A. Shillington, San Clemente, Calif.

[73] Assignee: Med-Safe Systems, Inc., Encinitas, Calif.

[21] Appl. No.: 747,256

[22] Filed: Jun. 21, 1985

[51] Int. Cl.⁴ .............................................. B65D 25/00
[52] U.S. Cl. ................................. 206/366; 206/63.5; 220/307
[58] Field of Search .................. 604/403, 110, 241; 220/307; 206/365–366, 63.5

[56] References Cited

U.S. PATENT DOCUMENTS

| | | | |
|---|---|---|---|
| 819,678 | 5/1906 | Simmons | 206/63.5 |
| 1,088,962 | 3/1914 | Bostwick | 206/63.5 |
| 4,375,849 | 3/1983 | Hanifl | 206/366 |
| 4,452,358 | 6/1984 | Simpson | 206/366 |
| 4,454,944 | 6/1984 | Shillington et al. | 206/366 |
| 4,466,538 | 8/1984 | Gianni | 206/366 |
| 4,488,643 | 12/1984 | Pepper | 206/366 |
| 4,502,606 | 3/1985 | Shillington et al. | 220/229 |

Primary Examiner—C. Fred Rosenbaum
Assistant Examiner—Gene B. Kartchner
Attorney, Agent, or Firm—Baker, Maxham & Jester

[57] ABSTRACT

A closure top for a phlebotomy needle disposal container is rotatably mounted in the container for rotating about its axis and includes a hub wrench for engaging the hub of the needle on the syringe body and rotating the needle upon rotation of the closure for unscrewing the needle and removing it from the syringe body.

18 Claims, 6 Drawing Figures

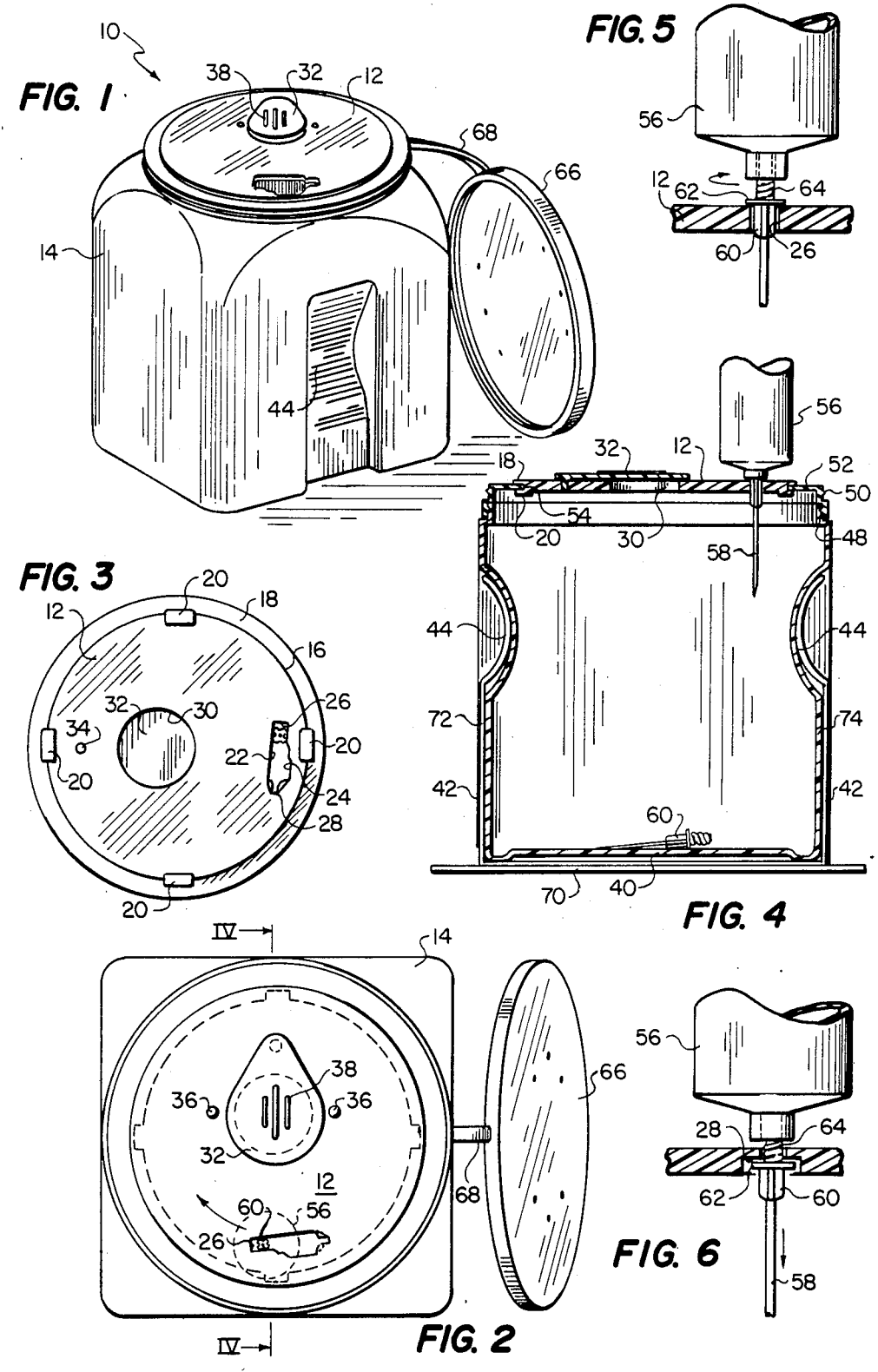

SWIVEL TOP CLOSURE FOR PHLEBOTOMY CONTAINER

BACKGROUND OF THE INVENTION

The present invention relates to disposable containers for medical devices, and pertains particularly to a rotatable top needle remover closure for a container.

Present day phlebotomy syringes for drawing samples of blood from patient's typically employ vacuum vials for drawing the sample of blood. The syringe device includes a tubular body member having a removable disposable needle in one end and being open on the other end for receiving the vacuum vial. The needle for such devices has a sharp point that extends into the body of the syringe for engaging and puncturing the vacuum vial to communicate therewith for communicating blood through the needle. Upon completion of the blood sample, the vial is removed and another may be inserted for taking further samples.

The syringe body of such devices is reusable with the needle being disposable. In order to reuse the body, the needle must be removed therefrom. The needles are threadably mounted in the body of the syringe and must be rotated several revolutions in order to disengage the threaded needle from the threaded bore of the syringe body.

The removal of the needle is a time consuming and sometimes hazardous process.

The present invention was devised to provide a quick and safe means for removing needles from syringe bodies.

SUMMARY AND OBJECT OF THE INVENTION

It is the primary object of the present invention to provide an improved means for removing needles from syringe bodies.

In accordance with the primary aspect of the present invention, a needle removal device for syringes comprises a rotatable closure for a container for mounting for rotation about its axis with a syringe wrench slot formed offset from the rotary axis of the closure for engagement with the hub of a needle for rotating the needle relative to the syringe body upon rotation of the closure.

BRIEF DESCRIPTION OF THE DRAWINGS

The above and other objects and advantages of the present invention will become apparent from the following description when read in conjunction with the drawings wherein:

FIG. 1 is a perspective view of a disposable container showing a closure in accordance with the invention installed;

FIG. 2 is a top view of the embodiment of FIG. 1;

FIG. 3 is a bottom plan view of the closure of FIG. 1;

FIG. 4 is a section view taken generally on line IV—IV of FIG. 2;

FIG. 5 is an enlarged detail view showing a needle being removed by rotation of the closure; and FIG. 6 is a view like FIG. 5 showing a final stage of removal of the needle.

DETAILED DESCRIPTION OF A PREFERRED EMBODIMENT

Referring to FIG. 1 of the drawing, a closure in accordance with the invention is shown installed in the opening of a disposable container, the entire assembly being designated generally by the numeral 10. The closure 12 comprises a flat circular disc that is designed to rotatably mount in a circular opening in a container. The closure is shown rotatably mounted in an opening of a container 14. The container may be disposable or reusable as will be further described.

The closure 12, as previously stated, comprises a flat circular disc defined by a circular peripheral edge 16 and having an overlapping radially extending flange 18 extending outward beyond the peripheral edge 16. The flange 18 is preferably formed on the top side of the closure for overlapping and engaging the wall area around an opening in a container. A plurality of tabs 20 extend outward from the inside surface of the closure disc overlapping the peripheral edge 16 or beyond the peripheral edge 16 for overlapping the inside surface of a wall surrounding a circular opening in a container. The construction of the closure is such that it is free to rotate with slight resistance within the opening within which it is mounted. The closure is designed to rotate about the central axis thereof.

A needle wrench in the form of an irregularly shaped slot or aperture is formed in the closure member 12 spaced from the central axis thereof for defining a crank arm as will be explained. The needle wrench comprises a slot having an enlarged central portion defined by a straight side 22 and an opposed curved portion 24 with one end 26 defined by stepped parallel sides defining a wrench for engaging and coupling the hub of a needle. The central enlarged portion of the slot is sufficiently wide to define an opening to enable a standard needle with its flange to fall therethrough. The wrench end 26 is designed to engage the hub of the needle for applying a rotatable torque thereto for removing the needle from the barrel. The needle engaging portion of the slot can have any suitable configuration for coupling to a needle hub. A slot 28 in the opposite end of the wrench assembly is formed by a portion of the disc that is less in thickness than the disc. This slot is designed to serve as a hook or puller for hooking the flange underneath thereof, as shown in FIG. 6, for applying axial force to the needle, if needed, for pulling it from the threaded bore of a barrel.

An additional opening 30, which may be a circular opening as shown in FIG. 3, may be formed in the closure for receiving other disposable items, such as barrels and the like. A pivoting closure tab 32 is pivotally mounted by a shaft 34 in the closure for pivoting to selected positions over the opening 30, as shown in FIGS. 2 and 3, for closing the opening or movable to positions to either side of the opening to provide access thereto. A pair of detect members 36 may be formed by knobs or bumps in the surface of the closure for holding the closure 32 in position. Flutes or ridges 38 may be formed on the top of the closure 32 for enabling ease of gripping and application of a side force thereto for pivoting the closure to its open position.

The closure is designed to be mounted in any container, however it is illustrated in conjunction with that is particularly suitable for disposal of phlebotomy needles. The container 14 is of a generally square boxlike configuration having a generally flat square bottom 40 with a first pair of opposite side walls 42 extending upward therefrom and having recesses 44 therein for purposes as will be described. The opposite sides 46 are generally flat square panels. The top of the container converges to a circular top with the arrangement shown illustrating a circular lip 48 having a circular closure rim 50 engaging lip 48 and having a inwardly directed wall 52 in which is formed a circular opening 54 within which the closure 12 is positioned. As best seen in FIG. 4, the flange 18 overlaps the wall 52 on the top side and the tabs 20 overlap the wall 52 on the inside, thus retaining the closure 12 in position in the opening of the container for rotation therein.

Referring to FIG. 4, there is illustrated a barrel 56 having a needle 58 mounted therein. The needle, as can be best seen in FIGS. 5 and 6, includes a fluted hub 60 with a flange 62 separating the hub from a threaded portion 64. The threaded portion 64 is designed to engage internal threads in a bore on the end of the barrel 56 for holding or securing the needle in place. The hub 60 is engaged by tools, such as a wrench slot, for removing the needle from the barrel.

When it is desired to remove the needle, the barrel is grasped in the hand and the needle extending into the wrench slot and positioned such that the wrench portion of the slot 26 engages the hub 60, as shown in FIGS. 3 and 4. Rotation of the closure in a clockwise direction, as shown in FIG. 2, utilizing the barrel as a crank handle applies a counter clockwise rotation to the needle relative to the barrel. As shown in FIG. 5, continued rotation of the closure around its axis results in the needle becoming unscrewed from the barrel as shown in FIG. 5. When the needle is completely unscrewed, the barrel is slipped toward the wide portion of the slot such that the flange portion of the needle can pass down through the slot into the barrel or container. Should for some reason the needle be still frictionally held to the barrel, the threaded portion of the needle can be slipped into the slot portion 28 such that the flange 62 is below the closure surface, as shown in FIG. 6, for gripping or hooking the end of the needle at the flange such that the barrel can be pulled from the needle, letting the needle fall into the bottom of the container.

The closure is designed to be flat, as illustrated, such that it can be used in conjunction with locking closures, such as disclosed in U.S. Pat. No. 4,502,606, granted Mar. 5, 1985 of which I am a co-inventor. These closures include a second cap or closure 66, which when the container is full and ready to be disposed of, can be locked in place over the closure such that access to the interior of the container is prevented.

The illustrated container is designed to be mounted in a holder for holding it in position such that the above described operation of removing a needle can be carried out by one hand. To this end a mounting bracket is illustrated in FIG. 4 which comprises a base member 70 designed to be attached to a table top or other suitable support surface. A pair of spring clip fingers 72 and 74 extend upward and include inwardly directed gripping tips 76 and 78 for extending into the recesses 44 of the container. Thus, the holder is designed to grip the container and hold it against rotation to permit rotation of the closure without having to hold the container.

While I have illustrated and described my invention by means of specific embodiments, it is to be understood that numerous changes and modification may be made therein without departing from the spirit and scope of the invention as defined in the appended claims.

I claim:

1. A needle removal closure comprising:
   a container having an upper edge portion defining an open end;
   a closure including an annular portion having a central opening fixed on said container upper edge portion;
   a disc rotatably mounted on said fixed annular portion within said central opening; and
   needle coupling means on said disc for coupling a needle thereto for rotation of said needle therewith for threadably removing said needle from a holder upon said rotation of said disc.

2. A needle removal closure according to claim 1 wherein said needle coupling means comprises an irregular opening through said disc said opening having a slot portion having parallel sides for engaging opposite sides of a hub of a needle.

3. A needle removal device according to claim 2 wherein:
   said disc defined by a peripheral edge;
   a circular flange extending radially outward beyond said peripheral edge on one side of said disc; and
   a plurality of tabs extending beyond said peripheral edge on the other side of said disc, said flange and said tabs for engaging opposite sides of said annular portion for rotatably mounting said disc in said central opening in said container.

4. A closure according to claim 1 comprising a circular opening in said rotatable disc, and pivoting closure means for said circular opening.

5. A closure according to claim 3 wherein said irregular opening is generally elongated and said coupling portion of said irregular opening is at one end of said opening, and a v-slot is formed at the other end thereof.

6. A closure according to claim 5 wherein said irregular opening has an enlarged portion near the center thereof.

7. A closure according to claim 6 comprising a circular opening in said closure adjacent the center thereof, and pivoting rotatable disc means for said circular opening.

8. A closure according to claim 1 wherein said coupling means comprises an elongated irregular slot formed in said rotatable disc offset from the axis thereof, said slot having an enlarged center portion, parallel sides at one end and a V-shaped other end.

9. A closure according to claim 8 wherein:
   said rotatable disc is defined by a peripheral edge and a pair of parallel planar faces;
   a radial flange extending outward beyond said edge from one of said faces; and
   a plurality of radially extending tabs extending outward from the other of said faces.

10. A needle removal closure assembly comprising in combination:
    a disposable container for disposing of used needles, said container having an upper edge portion defining an open end;
    a closure including an annular portion having a central opening fixed on said container upper edge portion;
    a disc rotatably mounted on said fixed portion within said central opening; and
    needle coupling means on said disc offset from the rotary axis thereof for coupling a needle thereto for rotation of said needle therewith for threadably removing said needle from a holder upon said rotation of said disc.

11. A needle removal closure assembly according to claim 10 wherein:

said needle coupling means comprises an irregular aperture in said disc, said aperture having an enlarged portion and a needle engaging coupling portion.

12. A needle removal closure assembly according to claim 11 wherein said coupling portion comprises a generally rectangular slot.

13. A needle removal closure assembly according to claim 12 comprising a flange engaging slot formed in said aperture.

14. A needle removal closure according to claim 13 wherein said aperture is elongated and said coupling slot is formed in one end thereof and said flange engaging slot is formed in the other end thereof.

15. A needle removal closure assembly according to claim 10 wherein said annular portion is defined by a generally circular top.

16. A needle removal closure assembly according to claim 15 wherein:
 said container has a generally square configuration but for said circular top; and
 further comprising releasable clip mounting means for releasably mounting said container on support means.

17. A needle removal closure assembly according to claim 16 wherein said container includes recesses in opposed walls thereof for receiving said clip mounting means.

18. A disposable container for disposing of hazardous objects, said container comprising:
 wall means defining a box-like container having an upper edge portion defining an open end;
 a closure including an annular portion having a central opening fixed to said container upper edge portion;
 a disc rotatably mounted on said fixed portion within said central opening for unlimited rotation relative to said container; and,
 an elongated irregular aperture formed in said circular disc offset from the rotary axis thereof, said aperture defining needle means at one end thereof for coupling a needle thereto for rotation of said needle therewith for threadably removing said needle from a holder upon said rotation of said disc relative to said box-like container, and pulling means at the other end for engaging a flange of a needle for pulling said needle from the threaded bore of a holder.

* * * * *